(12) United States Patent
Ligon et al.

(10) Patent No.: US 9,745,244 B2
(45) Date of Patent: Aug. 29, 2017

(54) CONTROL OF A PROCESS FOR THE PURIFICATION OF (METH)ACRYLIC ACID USING ON-LINE, NEAR IR ANALYSIS

(75) Inventors: Timothy D. Ligon, Saint Albans, WV (US); Olan S. Fruchey, Hurricane, WV (US); Christopher T. Reeves, Durham, NC (US); Fungau Ho, Charleston, WV (US); Roger L. Roundy, Rosharon, TX (US); William G. Etzkorn, Hurricane, WV (US); Mahmood N. A. Jawaid, Cross Lanes, WV (US); Patrick M. Wiegand, South Charleston, WV (US)

(73) Assignee: Arkeme Inc., King of Prussia, PA (US)

(*) Notice: Subject to any disclaimer, the term of this patent is extended or adjusted under 35 U.S.C. 154(b) by 580 days.

(21) Appl. No.: 13/121,046

(22) PCT Filed: Sep. 18, 2009

(86) PCT No.: PCT/US2009/057411
§ 371 (c)(1),
(2), (4) Date: Mar. 25, 2011

(87) PCT Pub. No.: WO2010/039451
PCT Pub. Date: Apr. 8, 2010

(65) Prior Publication Data
US 2011/0172462 A1    Jul. 14, 2011

Related U.S. Application Data

(60) Provisional application No. 61/101,743, filed on Oct. 1, 2008.

(51) Int. Cl.
*C07C 51/44* (2006.01)
(52) U.S. Cl.
CPC .................................. *C07C 51/44* (2013.01)
(58) Field of Classification Search
CPC ...................................................... C07C 51/44
USPC ............................................ 203/1, 3; 201/1
See application file for complete search history.

(56) References Cited

U.S. PATENT DOCUMENTS

| 4,272,247 | A | * | 6/1981 | Strain et al. ............ 436/55 |
| 4,540,831 | A | * | 9/1985 | Briggs ................... 568/697 |
| 5,910,607 | A | | 6/1999 | Sakakura et al. |
| 6,500,982 | B1 | | 12/2002 | Hale et al. |
| 6,646,161 | B1 | | 11/2003 | Eck et al. |
| 7,723,541 | B2 | | 5/2010 | DeCourcy et al. |
| 8,242,308 | B2 | | 8/2012 | Ho et al. |
| 2004/0226812 | A1 | | 11/2004 | Yada et al. |
| 2004/0267050 | A1 | | 12/2004 | DeCourcy et al. |
| 2006/0144686 | A1 | | 7/2006 | Yada et al. |

FOREIGN PATENT DOCUMENTS

| EP | 1493729 | | 1/2005 | |
| JP | 4187657 A | | 7/1992 | |
| JP | 2007-229459 | | 9/2007 | |
| WO | 2008/033687 | * | 3/2008 | ............ C07C 51/44 |

OTHER PUBLICATIONS

Ge et al. On-line monitoring of the distillates of a solvent switch process by near-infrared spectroscopy, Process Control and Quality, 11(4), 277-287 (1999).*
Ebert, J. NIR Spectroscopic Online Process Monitoring, LaborPracis, 24(4), 80-81, Apr. 2000.*
Sloley, "Effectively Control Column Pressure," Chemical Engineering Progress, Jan. 2001, pp. 38-48.*
"Proccess Control Using NIR Spectroscopy"; Polytee GmbH Analytic Application Note Spectroscopy, Nov. 2007—pp. 1-4.

* cited by examiner

*Primary Examiner* — Paul A Zucker
*Assistant Examiner* — Mark Luderer
(74) *Attorney, Agent, or Firm* — Lynn B. Morreale

(57) ABSTRACT

An improved process for the manufacture of technical grade (meth)acrylic acid, e.g., acrylic acid, the process comprising producing a hydrated reaction product from the gas-phase oxidation of at least one (meth)acrylic acid precursor, e.g., propylene, followed by first dehydrating and then concentrating the reaction product, the improvement comprising controlling at least one of the water, acetic acid and (meth) acrylic acid content of the reaction product during the purification of the reaction product using on-line, near IR spectroscopy.

3 Claims, 5 Drawing Sheets

CONTROL OF A PROCESS FOR THE PURIFICATION OF (METH)ACRYLIC ACID USING ON-LINE, NEAR IR ANALYSIS

CROSS-REFERENCE TO RELATED APPLICATIONS

This application is a national stage application under 35 U.S.C. §371 of PCT/US2009/057411, filed Sep. 18, 2009, which claims the benefit U.S. Provisional Application 61/101,743 filed Oct. 1, 2008, all of which are hereby incorporated by reference.

FIELD OF THE INVENTION

This invention relates to the manufacture of (meth)acrylic acid. In one aspect, the invention relates to the manufacture of (meth)acrylic acid in which (meth)acrylic acid is recovered and water and acetic acid is removed using a coupled, two tower purification system, while in another aspect, the invention relates to controlling the operation of the system by monitoring the water, acetic acid and/or (meth)acrylic acid content of the system. In still another aspect, the invention relates to monitoring these contents by using on-line, near infrared (IR) spectroscopy.

BACKGROUND OF THE INVENTION (Meth)acrylic acid and the commodity acrylate esters (methyl, ethyl, butyl, and 2-ethylhexyl) comprise one of the most versatile monomer series for controlling polymer performance characteristics. These monomers all have an alpha beta $(\alpha,\beta)$ unsaturated carboxyl structure and find extensive applications in surface coatings, adhesives and plastics. Furthermore, the sodium salt of polyacrylic acid is widely used as the superabsorbent polymer found in baby diapers. World production capacity for just crude acrylic acid is almost eight billion pounds per year.

The term "(meth)" indicates that the methyl substituted compound is included in the term. For example, the term (meth)acrylic acid represents acrylic acid and methacrylic acid, individually and collectively. While the process of the present invention can be employed in the production of acrylic acid and methacrylic acid, for the sake of simplicity the following description will refer to acrylic acid.

Currently, most, if not all, acrylic acid is produced commercially using a high temperature, two-stage air oxidation of propylene process. In the first stage propylene is oxidized with air to acrolein and then fed directly to the second stage in which the acrolein is further oxidized with air to acrylic acid. The catalyst used in each stage is a mixed metal oxide.

Acrylic acid is recovered from the product stream of the second stage reactor in a separation system. Various separation system designs exist. One such system comprises a quench tower coupled to an extractor which in turn is coupled to a series of distillation towers. The hot gases, e.g., gases at a temperature in excess of 230° C., exiting the second stage reactor are sent to the quench tower in which they are contacted with water. The hot gas condensibles, e.g., water, acetic acid, acrylic acid, etc., are separated from the hot gas non-condensibles, e.g., nitrogen, carbon oxides, etc. The off gases are sent to an incinerator and the cooled (e.g., a temperature of less than 230° C.) residue, liquid is sent to an extractor to remove the water. The extractor uses an organic solvent to extract the acrylic acid. The aqueous phase from the extractor is sent to a column in which residual solvent is azeotropically removed for recycle. The organic phase from the extractor is sent to the series of distillation towers from which crude acrylic acid is recovered.

As effective as these separation systems are, all are relatively expensive to build and operate, and all comprise a series of distillation columns that add to the complexity of their operation. Each tower requires the addition of fresh polymerization inhibitor at the top of the tower to prevent polymer fouling. The inhibitor is very expensive and adds to the production cost of acrylic acid.

In an effort to reduce costs and simplify operations, new separation systems have been proposed one of which is a coupled, two-tower system, i.e., a first or dehydration tower coupled to a second or finishing tower. The dehydration tower is equipped with a partial condenser which acts as a rectification system. The second or finishing tower is equipped with a reboiler and a total condenser, and it strips low-boiling and high-boiling impurities from acrylic acid product which is ultimately recovered as a side-draw.

Cooled (230° C. or less) gaseous reaction product from the second stage reactor is fed into a quench zone which can be located either within or without the dehydration tower (if located within the tower, then it is located in or near the base of the tower). Condensate from the finishing tower is used to quench the reaction gas into a concentrated acrylic acid solution. Vapor from the quench zone ascends into the dehydration tower. Acrylic acid is scrubbed out of this stream by the reflux descending from the top to minimize acrylic acid loss to the vent gas. Reaction water, acetic acid, light compounds and non-condensable gas are removed from the top of the tower some of which is recycled to the reactors and the remainder of which is purged to a thermal incinerator.

The bottom liquid stream from the dehydration tower is 70-100 wt % acrylic acid, 0-15 wt % water and 0-15 wt % acetic acid, and it is fed directly to the top or overhead of the finishing tower in which it is used as reflux. The finishing tower is operated under vacuum to prevent undesired polymerization of acrylic acid due to the relatively high (40° C. or greater) operating temperature of the tower. The overhead vapor is condensed and collected into a receiver, and the condensate is pumped and sprayed into the quench zone of the dehydration tower. Crude or technical grade (99+ wt %) acrylic acid is recovered as a vapor side-draw.

To obtain technical grade acrylic acid from the two-tower separation system described above, the water content of the tails stream from the dehydration tower should be between 1 and 15, preferably between 1 and 10 and more preferably between 3 and 5, wt %. If this water content is allowed to fall below 3 wt %, then the amount of acrylic acid loss in the overhead of the dehydrator is increased. If this water content is allowed to rise above 15 wt %, then the energy required to maintain reflux in the dehydrator is increased. Accordingly, tight control of this water content is important to the overall efficiency of the operation and to prevent undesirable polymerization and fouling of the equipment.

SUMMARY OF THE INVENTION

In one embodiment, the invention is a method for controlling the operation of a first distillation tower that is part of a coupled, two-tower system for the purification of (meth)acrylic acid, the method comprising the steps of:

A. Creating an electronic signal from an on-line, near infrared (IR) spectrometer, the signal based on at least one of the water, acetic acid and (meth)acrylic acid content of at least one of (i) a tails stream from the base of the first distillation tower, (ii) a condensed lights stream from a condenser coupled to and which receives an overhead stream from the first distillation tower, and (iii) an overhead stream from a second distillation tower that is coupled to and receives the tails stream from the first distillation tower;

B. Sending the electronic signal created in (A) to a means for controlling the operating temperature of the condenser that is coupled to the first distillation tower; and C. Increasing, decreasing or maintaining the operating temperature of the condenser based on the signal created in (A).

The means for controlling the operating temperature of the condenser is typically a microprocessor or similar device that receives the signal from the near IR spectrometer and, in turn, maintains or changes the operation of the device or devices that are responsible for the temperature control of the condenser. If, for example, the condenser is a shell-tube condenser and its operating temperature is a function of the rate of flow of cooling water through its shell, then the microprocessor or similar device can initiate a change to the rate of the flow of water through the shell to effect a change in the operating temperature (an increase in the rate of flow means a lower operating temperature and a decrease in the rate of flow means a higher operating temperature). If the signal created in (A) reports a water content that is less than a pre-determined setpoint, e.g., 4 wt % in the tails stream, then the operating temperature of the condenser is decreased, e.g., the flow of cooling water through the shell is increased. If the signal created in (A) reports a water content that is greater than the pre-determined setpoint, then the operating temperature of the condenser is increased, e.g., the flow of cooling water through the shells is decreased.

The water content of the tails stream from the base of the first distillation tower and the overhead stream from the second distillation tower are controlled such that they are in a range of 1 to 15, preferably in a range of 1 to 10 and more preferably in a range of 3-5, wt % based upon the total weight of the stream. The water content of the condensed lights stream from the condenser is controlled such that it is in a range of 80-95, preferably in a range of 80-90 and more preferably in a range of 82-90, wt % based upon the total weight of the stream.

The acetic acid content of the tails stream from the base of the first distillation tower and the overhead stream from the second distillation tower are controlled such that they are in a range of 1 to 20, preferably in a range of 1 to 15 and more preferably in a range of 1-10, wt % based upon the total weight of the stream. The acetic acid content of the condensed lights stream from the condenser is controlled such that it is in a range of 4-15, preferably in a range of 6-13 and more preferably in a range of 8-12, wt % based upon the total weight of the stream.

The (meth)acrylic acid content of the tails stream from the base of the first distillation tower and the overhead stream from the second distillation tower are controlled such that they are in a range of 70 to 100, preferably in a range of 75 to 100 and more preferably in a range of 80-100 wt % based upon the total weight of the stream. The (meth)acrylic acid content of the condensed lights stream from the condenser is controlled such that it is in a range of 1-10, preferably in a range of 1-8 and more preferably in a range of 3-7, wt % based upon the total weight of the stream.

In one embodiment the invention is a process of producing technical grade (meth)acrylic acid from a hydrated, gaseous reaction product obtained from the gas-phase oxidation of at least one (meth)acrylic acid precursor, the process comprising the steps of:

A. Cooling the gaseous reaction product;

B. Dehydrating the cooled gaseous reaction product in a first distillation tower to produce a gaseous overhead stream and a liquid tails stream;

C. At least partially condensing the gaseous overhead stream in a condenser having an operating temperature to form a condensate, and returning at least a portion of the condensate to the first distillation tower;

D. Creating an electronic signal from an on-line, near infrared (IR) spectrometer, the signal based on at least one of the water, acetic acid and (meth)acrylic acid content of at least one of (i) a tails stream from the base of the first distillation tower, (ii) a condensed lights stream from a condenser coupled to and which receives an overhead stream from the first distillation tower, and (iii) an overhead stream from a second distillation tower that is coupled to and receives the tails stream from the first distillation tower;

E. Sending the electronic signal created in (D) to a means for controlling the operating temperature of the condenser that is coupled to and receives the overhead stream from the first distillation tower; and F. Increasing, decreasing or maintaining the operating temperature of the condenser based on the signal created in (D).

In one embodiment, the gaseous reaction product is a product of a two-stage reaction system in which (meth)acrolein is produced from propylene and/or isobutylene and molecular oxygen, e.g., oxygen, oxygen-enriched air or simply air, in the first stage and (meth)acrolein is oxidized to (meth)acrylic acid in the second stage. In one embodiment, the water content of the dehydration tower tails stream is maintained by adjusting the operating temperature of the condenser that is coupled to and receives an overhead stream from the dehydration tower, a higher temperature to keep the water content from exceeding 15, preferably from exceeding 10 and more preferably from exceeding 5, wt %, and a lower temperature to keep the water content at greater than 1, preferably greater than 3, wt %.

In one embodiment the invention is an improved process for the manufacture of technical grade (meth)acrylic acid, the process comprising producing a reaction product from the gas-phase oxidation of at least one (meth)acrylic acid precursor followed by first dehydrating the reaction product and then concentrating the reaction product in a finishing zone, the reaction product comprising water, acetic acid and (meth)acrylic acid, the improvement comprising the steps of:

A. Creating an electronic signal from an on-line, near infrared (IR) spectrometer, the signal based on at least one of the water, acetic acid and (meth)acrylic acid content of at least one of (i) a tails stream from the base of the first distillation tower, (ii) a condensed lights stream from a condenser coupled to and which receives an overhead stream from the first distillation tower, and (iii) an overhead stream from a second distillation tower that is coupled to and receives the tails stream from the first distillation tower;

B. Sending the electronic signal created in (A) to a means for controlling the operating temperature of the condenser that is coupled to the first distillation tower; and C. Increasing, decreasing or maintaining the operating temperature of the condenser based on the signal created in (A).

The means for controlling the operating temperature of the condenser is typically a microprocessor or similar device that receives the signal from the near IR spectrometer and, in turn, maintains or changes the operation of the device or devices that are responsible for the temperature control of the condenser as previously described. The condensed product from the condensation zone is returned to a zone in which the hydrated reaction product is dehydrated.

In one embodiment the invention is a coupled, two-tower system for the dehydration of a reaction product obtained from the gas-phase oxidation of at least one (meth)acrylic acid precursor, the system comprising (A) a first distillation tower equipped with a base and top, (B) a condenser coupled to and in open communication with the top of the dehydration tower, the condenser equipped with means for controlling its operating temperature, (C) a second distillation tower equipped with a top, (D) means for transferring dehydrated reaction product from the base of the dehydration tower to the top of the finishing tower, e.g., a pipe, and (E) a near IR spectrometer comprising a probe or flow cell positioned on or within the means for transferring dehydrated product from the base of the dehydration tower to the top of the finishing tower. The probe is located within the pipe connecting the dehydration and finishing towers such that that dehydrated reaction product will interact with the probe to generate an electronic signal by the spectrometer that can be transmitted to the means for controlling the operating temperature of the condenser, e.g., a microprocessor that controls the flow rate of cooling water through the condenser. The probe is connected by any convenient means, e.g., fiber optics, to the spectrometer, e.g., a Guided Wave Lab 412 Laboratory Fiber Optic Spectrophotometer, which is typically located apart from the towers.

DETAILED DESCRIPTION OF THE PREFERRED EMBODIMENT

Figure 1:
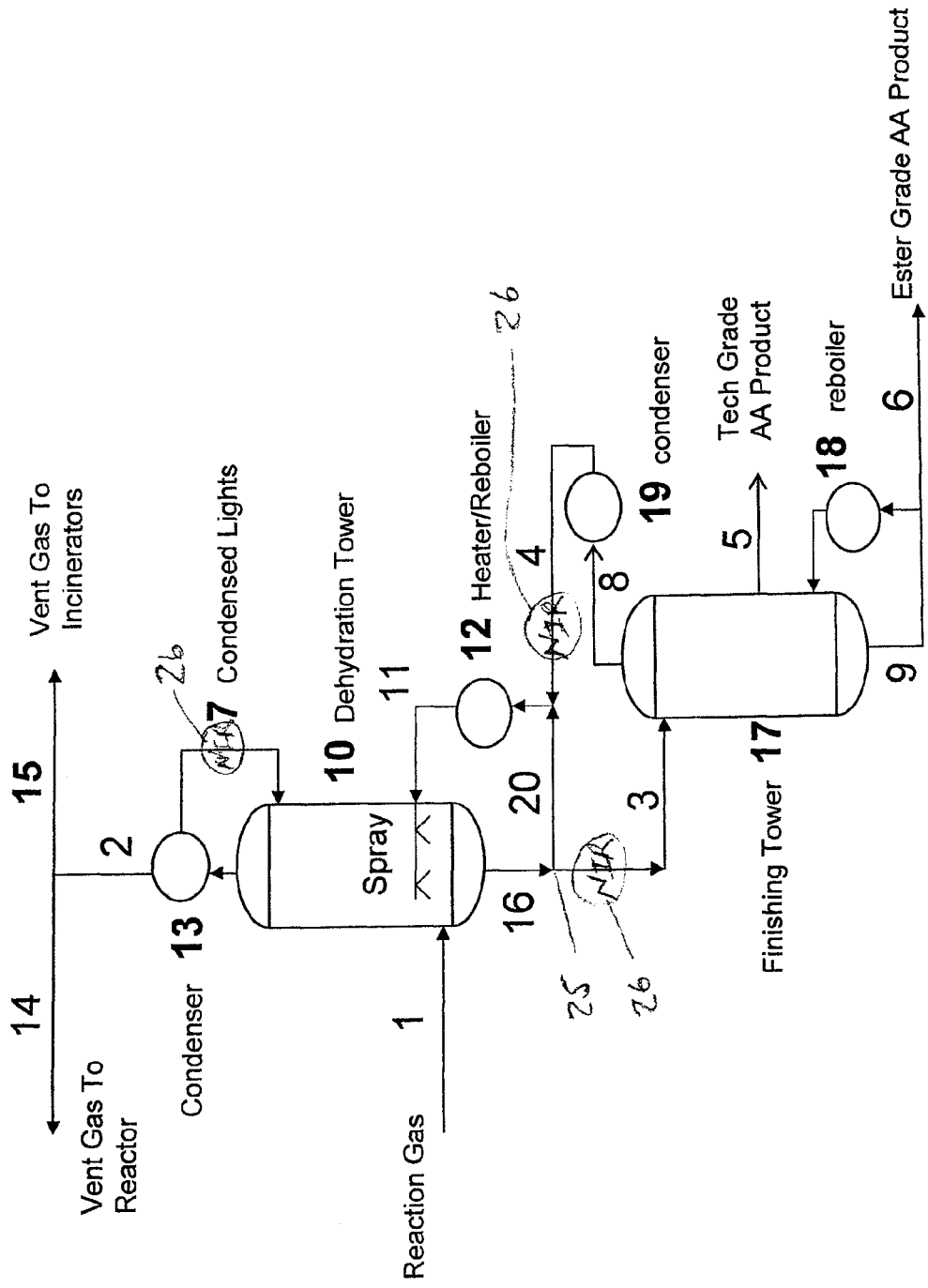
FIG. 1 is a schematic process flow sheet showing a configuration in which quenching (i.e., cooling) of a reaction product obtained from the gas-phase oxidation of at least one (meth)acrylic acid precursor is conducted primarily in the dehydration column.

All references to the Periodic Table of the Elements refer to the Periodic Table of the Elements published and copyrighted by CRC Press, Inc., 2003. Also, any references to a Group or Groups shall be to the Group or Groups reflected in this Periodic Table of the Elements using the IUPAC system for numbering groups. Unless stated to the contrary, implicit from the context, or customary in the art, all parts and percents are based on weight and all test methods are current as of the filing date of this disclosure. For purposes of United States patent practice, the contents of any referenced patent, patent application or publication are incorporated by reference in their entirety (or its equivalent US version is so incorporated by reference) especially with respect to the disclosure of synthetic techniques, definitions (to the extent not inconsistent with any definitions specifically provided in this disclosure), and general knowledge in the art.

The numerical ranges in this disclosure are approximate, and thus may include values outside of the range unless otherwise indicated. Numerical ranges include all values from and including the lower and the upper values, in increments of one unit, provided that there is a separation of at least two units between any lower value and any higher value. As an example, if a compositional, physical or other property, such as, for example, temperature, etc., is from 100 to 1,000, then the intent is that all individual values, such as 100, 101, 102, etc., and sub ranges, such as 100 to 144, 155 to 170, 197 to 200, etc., are expressly enumerated. For ranges containing values which are less than one or containing fractional numbers greater than one (e.g., 1.1, 1.5, etc.), one unit is considered to be 0.0001, 0.001, 0.01 or 0.1, as appropriate. For ranges containing single digit numbers less than ten (e.g., 1 to 5), one unit is typically considered to be 0.1. These are only examples of what is specifically intended, and all possible combinations of numerical values between the lowest value and the highest value enumerated, are to be considered to be expressly stated in this disclosure. Numerical ranges are provided within this disclosure for, among other things, the amount of water in the dehydrated reaction product, temperature and other process parameters.

The term "comprising" and its derivatives are not intended to exclude the presence of any additional component, step or procedure, whether or not the same is specifically disclosed. In order to avoid any doubt, all compositions claimed through use of the term "comprising" may include any additional additive, adjuvant, or compound whether polymeric or otherwise, unless stated to the contrary. In contrast, the term, "consisting essentially of" excludes from the scope of any succeeding recitation any other component, step or procedure, excepting those that are not essential to operability. The term "consisting of" excludes any component, step or procedure not specifically delineated or listed. The term "or", unless stated otherwise, refers to the listed members individually as well as in any combination.

"Technical grade acrylic acid" and like terms refers to a reaction product, typically after undergoing at least some purification, that contains at least 98.5% acrylic acid by weight, preferably contains at least 99 wt % acrylic acid, and more preferably at least 99.5 wt % acrylic acid. Furthermore, the reaction product contains less than 0.5 wt % water and less than 0.4 wt % acetic acid, preferably contains less than 0.3 wt % water and less than 0.2 wt % acetic acid, and more preferably contains less than 0.15 wt % water and less than 0.075 wt % acetic acid.

For the purposes of the invention, the terms "light" and "light compound" and their plurals refer to a compound or compounds having a boiling point or boiling points below the boiling point of the desired product. For example, water is an example of a light compound when the desired product is acrylic acid. A lights stream contains at least one light compound.

Similarly, the term "heavies" for the purposes of the invention means compounds having a boiling point above the boiling point of the desired product. Oligomers of acrylic acid and well known Michael addition products are examples of heavies when the desired product is acrylic acid.

"Separation system" and like terms refers to the equipment comprising dehydration and finishing columns and associated equipment, e.g., condensers, reboilers, piping, pumps, valves, surge tanks, monitors and the like as described below and/or used in the process of the invention.

"Reaction mixture", "reaction mass" and like terms means the combination of materials necessary or ancillary to a reaction, typically under reactive conditions. Over the course of a reaction, a reaction mixture converts into a product mixture. Depending upon the moment in time in which the reaction mixture is characterized and other factors such as whether the process is batch or continuous, the physical state of the starting and product materials, etc., it will or can contain the reactants, catalyst, solvent, processing aids, products, byproducts, impurities and the like.

"Reaction product", "product mixture" and like terms means the combination of materials resulting from subjecting a reaction mixture to reaction conditions. A product mixture will always contain some product and/or byproduct and depending upon a multiplicity of factors (e.g., batch versus continuous, physical state of the starting materials, etc.), it may or may not contain unreacted starting materials, catalyst, solvent, processing aids, impurities, and the like. The typical reaction product of the propylene oxidation reaction (the reaction conducted in the first stage reactor) will contain acrolein, acrylic acid, water, oxygen and unreacted propylene. The typical reaction product of the acrolein oxidation will contain acrylic acid, acetic acid, unreacted acrolein, water and oxygen.

"Reaction conditions" and like terms generally refer to temperature, pressure, reactant concentrations, catalyst concentration, cocatalyst concentration, product and by-product (or solids) content of the reaction mixture (or mass) and/or other conditions that influence the properties of the resulting product.

"Oxidation conditions" and like terms means the temperature, pressure, reactant concentrations, catalyst concentration, cocatalyst concentration, product and by-product (or solids) content of the reaction mixture (or mass) and/or other conditions necessary to convert, for example, propylene and oxygen to acrolein, or acrolein and oxygen to acrylic acid.

"Coupled, two-tower separation system", "coupled distillation columns", "coupled distillation towers" and like terms refers to two distillation towers or columns connected in a manner such that the tails stream from the first column is fed directly or indirectly into the top of the second column while the overhead stream of the second column is fed directly or indirectly into the base of the first column. "Indirectly" means that the stream first passes through at least one other vessel, e.g., a surge tank and/or heat exchanger, before entering the first or second column.

The feed stream to the process of the invention preferably is a gaseous reaction product. Preferably, this product results from the two-step catalytic vapor phase oxidation of at least one (meth)acrylic acid precursor, such as propylene in the case of acrylic acid or isobutylene in the case of methacrylic acid. The second step of the oxidation process typically converts an intermediate, such as (meth)acrolein, to the final product. This well-known oxidation process is widely used commercially. See U.S. Pat. No. 6,646,161 B1, the teachings of which are incorporated herein by reference, for a discussion the composition of the hot gaseous reaction mixture.

The first step of the process of the invention is to cool the gaseous reaction mixture. The gaseous reaction mixture typically is superheated as it comes from the reactor system, in other words, it contains more heat (energy) than the amount of heat required to vaporize the mixture. In one embodiment of the invention, the cooling step removes essentially the entire amount of superheat from the gaseous reaction mixture. For example, the hot acrylic acid reactor outlet gases and vapors are cooled to less than 260 C (~500 F) in a shell and tube heat exchanger, and then enter a quench system where the gases are cooled by direct contact with an acrylic acid containing liquid at a temperature less than 120 C (~250 F), preferably less than 110 C (~225 F) and more preferably under 100 C (~212 F). The difference in temperature between the temperature of the bottoms of next distillation column and the temperature of the outlet gases and vapors leaving the quench system is less than 28 C (~50 F), preferably less than 5 C (~10 F) and more preferably less than 3 C (~5 F).

The cooling step can be conducted directly or indirectly in one or more pieces of equipment. For example, the cooling of the gaseous reaction mixture can be initiated in a quench or flash vessel, or can be integrated into the bottom of the dehydration column, with or without column internals. The quench system may contain one or more spray nozzles in one or more locations to distribute the acrylic acid containing quench liquid across the cross sectional area through which the hot gases and vapors must pass. The nozzles may be oriented to spray quench liquid horizontally to the flow path of the hot gases and vapors, or axially in the direction of the flow of the gases and vapors, or against the direction of the flow of the gases and vapors, or any combination of these options. The orientation of the external quench system can be 0-90 degrees relative to the horizontal, preferably 90 degrees or vertical with the hot gases and vapors and quench liquid flowing downwards and co-currently towards the dehydration column inlet. The quench system may also contain one or more trays whose type is not particularly limited or packing or combination of the two. Preferably, the cooling step is initiated or primarily conducted external to the dehydration column.

The acrylic acid containing quench liquid may be comprised of a liquid circulated from the next distillation tower bottoms, combined with one or more acrylic acid containing streams filtered to remove insoluble solids, heated in a heat exchanger to control the temperature, and returned to the quench system. The ratio of the circulated liquid flow rate from the distillation tower bottoms to the combined flow rates of the one or more process streams added to the circulated liquid flow rate from the distillation tower bottoms is 1:1, preferably 5:1 and more preferably 9:1.

In its most simple form, the quench system may be a section of pipe before the pipe enters the dehydration column in which the hot gases and vapors pass through a radial splashing shower of acrylic acid containing liquid accomplished by impinging two opposing axial jets of acrylic acid containing liquid in or near the center of the pipe section. Preferably, a target metal plate with a diameter 0.1 to 0.5 times the internal diameter of the pipe section, preferably 0.2 times the internal diameter of the pipe section, may be located at the center of the two jets and used as an impingement device to create the radial splashing shower of acrylic acid containing quench liquid. Advantageously, a two-phase flow vapor/liquid disengagement device is provided internal to the dehydration column at a point of entrance for the quenched reaction gases and vapor and quench liquid. This device can be of any design that will reduce the velocity of the quenched vapors and gases and quench liquid, separate the majority of the quench liquid from the cooled reaction vapor and gases, and distribute the majority of the cooled reaction vapors and gases across the cross sectional area of the dehydration column. In its simplest form, it is comprised of an impingement baffle located at the inlet of the dehydration column for the quenched reaction vapors and gases and the quench liquid.

One unique feature of this purification system is that the feed to the dehydrator is a two phase feed (i.e. gas and liquid). This is the result of the cooling step. A normal distillation tower has only one phase feed (i.e. a liquid or a gas).

In the process of the invention, the at least partially cooled reaction mixture is dehydrated. The dehydration preferably is conducted in a dehydration column. The dehydration column functions to remove the majority of water from the incoming gaseous reaction mixture. Advantageously, the dehydration column is operated such that there is a bottoms stream and an overhead stream. In a preferred embodiment of the invention, at least a portion of the overhead stream is condensed and is returned as a reflux liquid to the dehydration column.

In one embodiment of the invention, essentially all noncondensibles and lights exit the dehydration column in the overhead stream. Examples of noncondensibles present during the production of acrylic acid include nitrogen, oxygen, carbon monoxide, carbon dioxide, and unreacted hydrocarbons such as propane and propylene. Advantageously, the entire overhead stream is introduced into a condenser, and at least a portion of the lights are condensed and returned to the dehydration column as a reflux stream. This condenser can be internal or external to the dehydration column, and it can be of the shell and tube or direct contact type design (e.g., quench cooler). Part of the gas stream from the condenser is recycled to the reactors and the remainder is sent to an incinerator. To further recover acrylic acid as a valuable product, the recycle gas can be sent to a condenser before it is fed to the reactors.

The dehydration column functions, at least partially, as a distillation column. However, as noted above, the dehydration column can also serve as a contacting zone for cooling of the gaseous reaction mixture. Preferably, the pressure in the dehydration column is no higher than the pressure of the incoming gaseous reaction mixture. Preferably the temperature of the bottoms stream from the dehydration column is less than about 120° C. The temperature of the overhead stream from the dehydration column is at least about 40° C.

The vent stream from the overhead condenser on the dehydration column is at least partially recycled to the reactor system. In one embodiment of the process, a portion of the vent stream is removed from the separation system as a purge stream.

The bottoms stream from the dehydration column advantageously is sent to a second column, except that a portion of this stream can be employed to cool the gaseous reaction mixture. In one embodiment of the invention, a portion of the bottoms stream from the dehydration column is sent to a heat exchanger, which can be a reboiler. However, it is noted that the process can also be operated under conditions such that the heat exchanger is a cooler, depending on whether the process design requires heating or cooling. In a preferred embodiment of the invention, a portion of the bottoms stream from the dehydration column is fed to a second column (also known as a finishing tower). Advantageously, the feed point is the top of the second column. The second column preferably is a distillation column and is used in conjunction with a reboiler and a condenser.

The means for conveying the bottom or tails stream from the base of the dehydration tower to the top of the finishing tower, e.g., a pipe, is fitted with a probe (also known as a flow cell) of an on-line, near IR spectrometer (the spectrometer itself typically located apart from the towers, e.g., in a control room). The probe is fitted on or within the pipe in such a manner that it can contact or otherwise interface with the tails stream to obtain information as to the water content of the stream. This information is then sent to the spectrometer by any convenient means, e.g., fiber optic cable, wireless transmission, etc., and the spectrometer generates a spectrum of light absorbance versus wavelength. This spectrum allows for the determination of the water content of the sampled stream. A signal is generated by the spectrometer based upon the spectrum, and the signal is sent to the means for controlling the operating temperature of the condenser. This means is typically a microprocessor in which the signal is compared against a pre-determined setpoint or standard and depending upon the comparison, the operating temperature of the condenser is increased, decreased or maintained steady. Typically, if the signal is higher or lower than the setpoint, then the microprocessor sends a signal to the condenser to change its operating temperature (usually by changing the flow rate of cooling water through it). If the signal from the spectrometer is the same as the setpoint, then the microprocessor either does not send a signal to the condenser or it sends a signal that instructs no change to the operating temperature of the condenser. This mode of operation works the same whether the probe is measuring the water, acetic acid or acrylate acid content of the tails stream, the overhead stream of the finishing tower or the condensed lights stream of the condenser.

As just noted, the near IR water analysis produces a fingerprint of the current composition of the sampled stream in the form of a spectrum of light absorbance versus wavelength. The analysis for water is made by an on-line, near IR spectrometer in the wavelength range 800-2650 nanometers (nm), preferably 1000-2100 nm, to determine a series of absorbances that are correlatable to water (or acetic acid or acrylic acid), and then preferably comparing the absorbances, or a function of them, or the amount of water (or acetic acid or acrylic acid) corresponding to the absorbance with a desired value, and then adjusting the separation process based in the comparison to minimize the difference from the desired value. This adjustment is typically made by adjusting the operating temperature of the condenser that receives the overhead stream from the dehydrator tower. The wavelength 1000-2100 nm range also allows for the use of fiber optics to connect the probe to the spectrometer. The probe or flow cell is placed at the process analysis point and light is brought to and from the sample point using low-hydroxyl silica fiber.

The particular absorbance(s) in the near IR may be in the region of the 1000-2650 nm, but it is preferably in the region of 1400-1500 nm, 1100-1350 nm or 1600-1700 nm; absorbances are especially preferred in the 1100-1700 nm region. A single absorbance in the near IR region may be used, but advantageously the absorbances of least 2 and possibly many hundreds of wavelengths are chosen. The absorbances may be chosen because of known absorption of water at that wavelength or may be chosen statistically by regression analysis, e.g., partial least squares (PLS) or multi-linear regression MLR because of their correlation with the water amount. The number of wavelengths chosen is limited in MLR by the number of independent calibration standards available, but PLS does not have this limitation and is therefore the preferred type of regression analysis.

The absorbances may be measured on samples of the appropriate stream, these samples being taken from the stream or volume through a pipe acting as a spectroscopy analysis cell, e.g., containing a near IR probe. Especially, the absorbance may be measured directly on the appropriate stream or volume, e.g., via a probe inserted directly into the stream or volume, in which case the absorbance is measured effectively on-line and in real time. The cell path lengths vary according to the wavelength of the absorbance, being, e.g., 2 millimeter (mm) for wavelength of 1600-2650 nm and 5 mm for wavelengths of 800-1500 nm. The near IR radiation source and detector in the near IR spectrophotometer may be close to the cell, but are preferably spaced from it, e.g., by 1-1000 m in particular 5-100 m, the radiation passing to and from the cell by way of an optical waveguide, e.g., one or more optical fibers. The optical fibers transmit the near IR radiation of the chosen wavelength and may consist of zirconium fluoride for wavelengths of 2000-2650 nm, and silica or glass for lower wavelengths. The absolute size of the absorption is reduced as the wavelength chosen becomes smaller. Preferably the 1100-2100 nm region is chosen with optical fibers, e.g., of silica, quartz or glass leading to a spectrophotometer 5-100 m away from the cell. The near IR spectrophotometer is preferably able to scan with a resolution of less than 10 nm, e.g., less than 2 nm. The radiation from source to cell to detector may pass to only one cell or may, via a multiplexer, be passed in parallel to a series of cells with parallel return to the detector.

The absorbance signal may be converted to a figure for the water content either directly by the Beer Lambert Law of absorbance proportional to concentration of absorbent, if at that wavelength, the simple linear relationship applies. Otherwise the relationship may be determined by calibration with if required statistical analysis of the data on the reaction with a variety of water contents (measured independently by standard means) and hence a variety of absorptions; the statistical methods may be by MLR or PLS or other regression techniques. Statistical analysis may also be used to determine the optimum wavelength(s) to choose correlatable to the water content. If desired the absorbance data may be mathematically processed; functions of the absorbances such as derivatives e.g. first, second or third derivatives may be used in the statistical analysis. The relationship between absorbance (or function thereof e.g. derivative) and water content is thus found and may involve more than one wavelength, with a regression equation having linear terms, quadratic terms and/or reciprocal terms. An example of such an equation is $$[\text{Water content}] = A_o + \Sigma A_i \lambda_i$$

where $A_o$ is a constant and $A_i$ is multiplier constant for the absorbance (or derivative) $\lambda_i$ and i varies from 1 to the number of wavelengths used.

A similar monitoring scheme can be described in which acrylic acid or acetic acid is determined by near IR. The method is identical to that described for water, with the exception that the wavelength regions are chosen to optimize the regression equation for the component of interest. In addition, the wavelength regions can be chosen to optimize for the concentration range of the component of interest. The wavelength regions can also be optimized to minimize interference from other components and the concentration range of these other components also affect the choice of preferred wavelengths.

For example, as previously stated, water can be determined using the entire wavelength range from 1000 nm to 2100 nm. However, optimal wavelength regions are preferred. For water in the concentration range 1% w/w to 15% w/w the set of wavelengths composed of the regions 1404-1429 nm and 1459-1474 nm are preferred. For water in the concentration range of 80% w/w to 95% w/w the set of wavelengths composed of the regions 1127-1132 nm, 1145-1148 nm, 1330-1347 nm, 1684-1695 nm, and 1704-1707 nm are preferred.

As another example, if it is desired to monitor the level of acetic acid and use this concentration in a control scheme, the entire wavelength range of 1000-2100 nm can be used. However, an optimal subset of these wavelengths is preferred. For acetic acid concentrations in the range 1% w/w to 20% w/w, in the presence of water in the range of 1% w/w to 15% w/w/ the set of wavelengths composed of the regions 1260-1263 nm, 1271-1274 nm, 1658-1665 nm, 1727-1733 nm, 1736-1745 nm, and 1761-1786 nm is preferred for the determination of acetic acid. For similar acetic acid levels in the presence of water in the concentration range of 80% w/w to 95% w/w, the set of wavelengths composed of the regions 1130-1135 nm, 1610-1615 nm, and 1652-1655 nm is preferred.

As another example, acrylic acid concentration may be determined by NIR and its concentration used in a control scheme by using the entire wavelength range of 100-2100 nm in the regression equation. However, an optimal subset of preferred wavelengths for determination of acrylic acid in the range of 70% w/w to 100% w/w in the presence of water in the range of 1% w/w to 15% w/w is composed of the set of wavelengths in the region 1617-1680 nm. For determination of acrylic acid in the concentration range 3% to 7% w/w in the presence of water in the range of 80% w/w to 95% w/w the optimum subset of wavelengths composed of the regions 1012-1020 nm, 1580-1621 nm, and 1721-1723 nm is preferred.

In the above calibration determination of the relationship, the reaction conditions e.g. temperature, pressure, feed rate(s), ratios of feeds, space time yield, and analysis of catalyst are kept constant, while the water content is systematically varied. The conditions must then be controlled at these conditions for the calibration equation to be applicable. The calibration equation may as an alternative be determined with random variations in the conditions. Calibrations determined in this manner do not need to have the conditions controlled as long as they remain within the ranges used for calibration.

With the above prior determination of the relationship, the method of the invention may be applied to a reaction under the same conditions, to obtain the absolute water content of the analyzed stream. If the obtained value deviates from the desired value then the rate of water addition is adjusted to minimize the difference from that desired value. Deviations are kept usually below 10% from the desired value, in particular below 5% from that value.

If desired, the absolute water content need not be determined, so long as a function related thereto is obtained and the process controlled to minimize deviations in the value of that function, e.g. with the size of deviations as shown above. The deviations may be determined by computer and the adjustments to control the process and minimize it may also be made by computer.

The spectrometer computer is connected to a microprocessor (otherwise known as a process control computer) that receives a water content signal from the spectrometer computer and compares it against a predetermined standard. If the signal matches the standard, then the microprocessor either sends a signal to the condenser that receives the overhead stream from the dehydration tower to maintain its current operating temperature, or it does not send a signal. If the signal does not match the standard, then the microprocessor sends a signal to the condenser to either raise or lower the temperature depending if the water content signal is reporting too much or too little water in the dehydrated reaction product. The hardware and software for this feedback loop is well known in the art.

As with any spectroscopic measurement, the medium being analyzed, e.g., the tails stream from the dehydration tower, is preferably homogeneous for best results. Placement of the probe is preferably in a position where the stream is without bubbles and the pipe or other vessel is always full of liquid. Methods exist to minimize the effect of inhomogeneity, but the better method is to eliminate the inhomogeneity itself, e.g., plumb the probe or flow cell into a slipstream of the process. This also allows the probe or flow cell to be easily isolated for cleaning or other maintenance.

The second column has two product streams, i.e., a side stream and a residue stream. The difference between these streams is the heavy ends content. The two key heavy end components in these streams are the acrylic acid dimer, i.e., Michael addition product, and maleic acid/anhydride. As the take-off ratio of side stream to residue stream increases, these heavy ends concentrate in the residue stream relative to the side stream. The residue stream (sometimes referred to as ester grade acrylic acid) is typically unsuitable as a feed to a melt crystallizer, i.e., a glacial acrylic acid unit, due to the high dimer, inhibitor and maleic acid/anhydride content. This stream, however, can be used as feed for an acrylate ester unit especially if the ester unit is equipped with a dimer cracker. The dimer cracker unit in a butyl acrylate (or other acrylate ester) unit converts most of the dimer back to acrylic acid which is converted into butyl acrylate, i.e., the acrylic content of the dimer is recovered as useable acrylic acid raw material. The maleic acid/anhydride in the residue product reacts with butanol forming esters which are high boilers and easily removed from the butyl acrylate product in the purification train. For esters such as methyl acrylate and ethyl acrylate, the cracking of the dimer can be done in situ by providing sufficient residence time and temperature in the reactor volume in the base of the reaction/esterification tower.

The side stream material which is referred to as technical grade acrylic acid can be fed to a melt crystallizer unit for glacial acrylic acid production or used as feed to any acrylate ester unit. One process enhancement for the finishing tower is to equip its reboiler recirculation loop with a dimer cracker. In this scenario the cracker residue stream is very concentrated and most (>95%) of the acrylic acid product is taken as the side stream product (i.e. technical grade acrylic acid). The highly concentrated residue stream from the cracker can then be incinerated to regain fuel value.

In one embodiment the overhead stream from the second column is sent to a condenser. Preferably, the condenser is operated as a "total condenser" in that essentially the entire overhead stream is condensed. However, it is possible to remove a purge stream of noncondensible compounds from this condenser. Advantageously, the condensate from the second column condenser is used to cool the reaction gas mixture, either as is or after additional heat exchange.

The bottoms stream from the second column advantageously is at least partially sent to the second column reboiler. The remainder of the bottoms stream can be incinerated or can be further treated according to known methods; for example, the bottoms stream can be sent to an acrylates ester production unit or can be subjected to a cracking step in which Michael addition compounds are treated to recover acrylic acid, which can then be recycled. In one embodiment the bottoms stream contains the majority of the acrylic acid to be recovered from the process. However, in a preferred embodiment the majority of acrylic acid is recovered from a side draw stream from the second column.

In view of the fact that the side stream is in the second column, the separation process removes product acrylic acid at a point below the point where the gaseous reaction product is fed to the separation system, i.e. the product stream is removed below the feed in the separation system.

The temperature and pressure in the second column are not particularly critical, and can be determined according to design considerations well-known to those skilled in the art. Preferably, the second column is operated below the operating pressure of the dehydration column. Preferably, the second column is operated at subatmospheric conditions. This has the advantage of allowing the second column to operate at lower temperatures, thereby minimizing undesired dimer, oligomer and/or polymer formation. Advantageously, the temperature of the overhead stream as it leaves the second column is from 40 to 90° C. when producing acrylic acid and operating the second column at a head pressure of from 40 to 500 mm Hg. The temperature of the bottoms stream from the second column advantageously is from 60 to 120° C. when producing acrylic acid.

Figure 5:
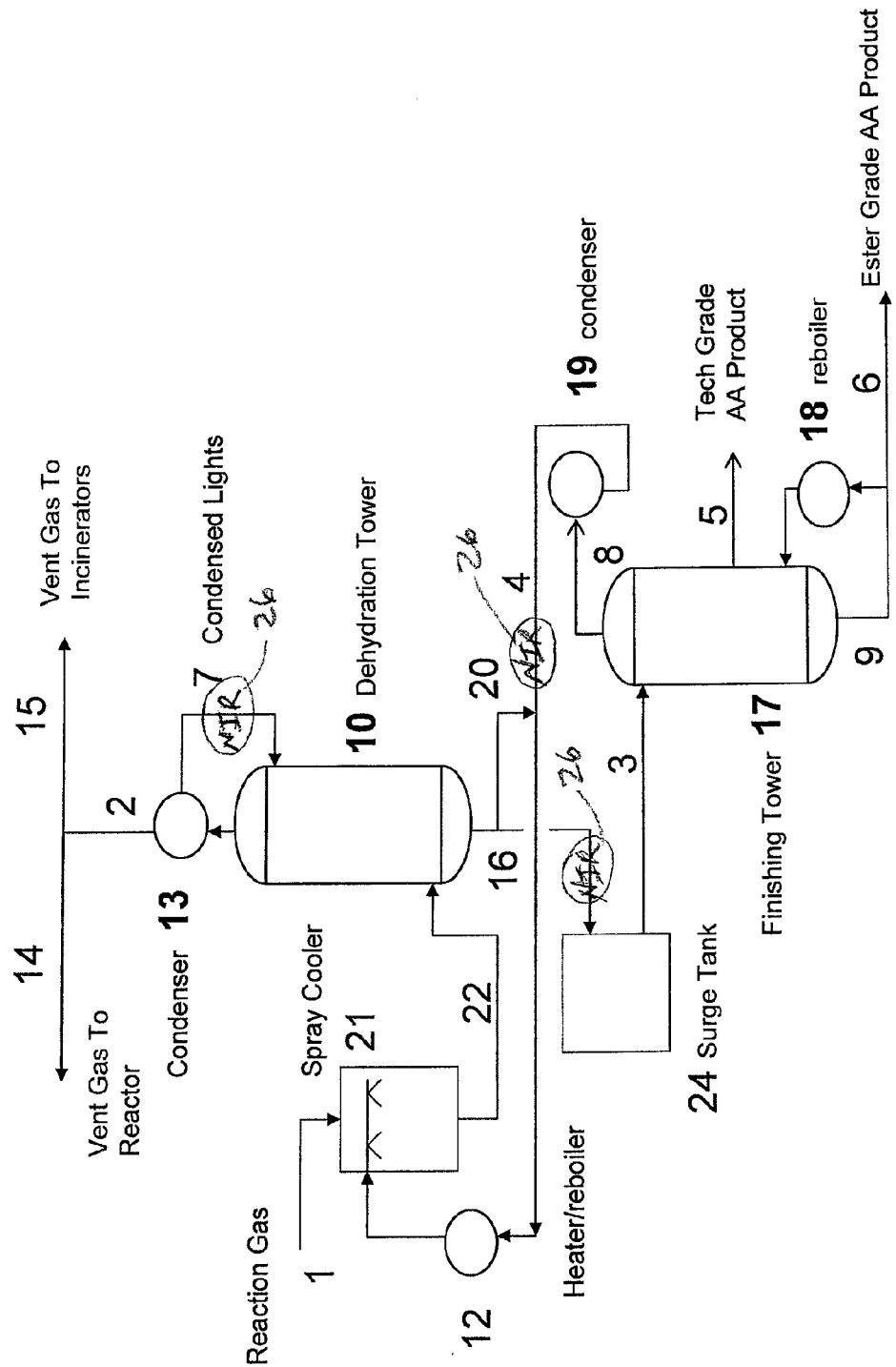
FIG. 5 is a schematic process flow sheet showing a configuration in which at least a portion of the tails stream from the dehydration tower are passed through a surge tank before entering the finishing tower.

The design details of the dehydration column and of the second column, including their operating conditions such as temperatures, pressures, flow rates, equipment sizing including column height and diameters, choice of materials of construction, arrangement and choice of type of auxiliary equipment such as heat exchangers and pumps, choice and arrangement of column internals, and location of piping including take-off streams, can readily be determined by those skilled in the art according to well-known design considerations. Examples of distillation column configurations that can be used in the process of the invention include, for example, packed columns, tray columns, divided wall columns, multi-stage devolatilizers, and the like. Any type of tray can be employed, including bubble trays, valve trays, cross flow trays, dual flow trays, and combinations thereof. Similarly, if packing is employed, any type of packing can be used, including randomly- or regularly-spaced packing. In a preferred embodiment of the invention, the dehydration column comprises packing in its upper section and trays in the lower section. The lower section provides for direct cooling of the incoming gaseous reaction mixture. The number of theoretical stages for the dehydrator and finishing columns are not specifically limited. Preferably 5 to 50 theoretical stages for the dehydrator are used, and more preferably 20 to 30 theoretical stages. Preferably 5 to 30 theoretical stages are used for the finishing column, more preferably 8 to 20 theoretical stages. Surge tanks optionally can be employed within the separation system such as, for example, at one or more locations between the dehydration column and the second column as shown in FIG. 5.

In a preferred embodiment the process equipment is at least partially constructed using copper or copper-containing alloys, such as various alloys sold under the mark Monel™. These and other copper-containing alloys provide polymer inhibition for acrylic acid as a result of copper dissolution in the presence of air. Unfortunately, the corrosion rate in the presence of hot streams containing maleic acid is too high for practical commercial use of these alloys in the finishing column. However, the upper section of the dehydrator is essentially free of maleic acid (due to its high boiling point) and this region of the dehydrator can use trays or packing constructed from Monel™ copper-containing alloys as part of a fouling abatement scheme. The use of such packing in this region of the dehydrator provides a self-inhibiting surface which helps alleviate fouling potential due to poor inhibitor distribution in the packing. Other metals, such as stainless steel including 316 stainless steel, can also be employed as the material(s) of construction for the process equipment by using criteria well known to those skilled in the art.

The use of inhibitors is preferred in the process regardless of the choice of materials of construction. Various compounds are well known to inhibit the reaction of acrylic acid, and are commercially available. Examples of preferred inhibitors include soluble manganese ions, soluble copper ions, 2,2,6,6-tetramethyl-1-piperidinyloxy (TEMPO) and related compounds such as 4-hydroxy TEMPO. Combinations of inhibitors can be employed. In a preferred embodiment a mixture of a source of soluble manganese ions, such as manganese acetate, and 4-hydroxy TEMPO are employed in the dehydration column as an inhibitor. 4-hydroxy TEMPO/manganese acetate is also the preferred inhibitor for the second column. An alternate inhibitor system that could be used in both columns is hydroquinone/manganese acetate. Molecular oxygen or air is preferably employed in the second column because oxygen is a known inhibitor. The inhibitor is employed in an amount sufficient to prevent or reduce the polymerization of acrylic acid, as is well known to those skilled in the art. Air injection is only required for the second column because the reaction gases fed to the dehydrator already contain oxygen in an amount sufficient for the inhibitor system. Typically, sufficient air is injected such that oxygen is present in the column in an amount of at least 0.1 volume percent relative to the amount of vapor in the column.

One technique frequently used industrially to minimize inhibitor cost is to recycle streams that have a high inhibitor concentration. In one embodiment the inhibitor is concentrated in the residue stream of the second column. Accordingly, a portion of this stream can be recycled to either or both the overhead of the dehydrator and/or the overhead of the second column.

Advantageously, an acrylic acid product stream is recovered from the second column as a side draw stream. The location of the side draw on the second column is a matter of design preference, and can be determined using design techniques well-known to those skilled in the art. Preferably, this point of removal is below the feed tray and 2 or 3 theoretical stages above the reboiler. The trays may be of any style design such as cross-flow or dual flow or any combination of the two. This process also works with packing or any combination of trays and packing. The acrylic acid product is removed from the side of the distillation tower as predominantly a vapor or a liquid. The apparatus for collecting the side stream is comprised of a nozzle and a vapor-liquid separation space where most liquid is separated by gravity from the vapor with or without an internal vapor or liquid collector. The liquid or vapor collector may comprise a pipe with one or more perforations, an inverted funnel, a funnel, a downcomer, a hat tray, an impingement baffle, a liquid distributor, a liquid collector, a baffle or any combination of these. The weight ratio of the side draw to bottom stream is preferably 75:25, or more preferably 95:5. However, advantageously, the side draw to bottom stream weight ratio can also be designed by one skilled in the art to be 25:75 or even 5:95. In a further embodiment, no side draw is taken and the entire acrylic acid product is taken in the bottoms stream. As a practical matter, the side stream is typically of better quality than the tails, i.e., the side stream contains less heavy components than does the tails.

One surprising advantage of the process is that the product stream is produced in high purity by a process that does not require an azeotropic solvent or other solvent. For example, the product stream advantageously contains at least about 98.5% acrylic acid by weight, preferably contains at least about 99% acrylic acid, and more preferably at least about 99.5% acrylic acid. Advantageously the product stream contains less than about 0.5% water and less than about 0.4% acetic acid, preferably contains less than about 0.3% water and less than about 0.2% acetic acid, and more preferably contains less than about 0.15% water and less than about 0.075% acetic acid. The process preferably can produce a product stream that is usable as technical grade acrylic acid without further separation processing.

One embodiment of the invention is shown in FIG. 1. Referring to FIG. 1, hot, gaseous reaction product feed stream 1 containing acrylic acid is introduced into the lower area of dehydration column (or tower) 10. Upon entering the dehydration column, the reaction product is contacted with, and cooled by, liquid 11 supplied from heat exchanger 12, which can be a cooler or a heater, but preferably is a heater. The contacting can comprise spraying, feeding the cooling liquid to a distillation tray or packing through which the hot reaction gaseous mixture rises, or a combination of these. The partially cooled reaction product flows up the dehydration column through internals (not shown) which can be trays or packing of any configuration, as is well known to those skilled in the art. As the cooled reaction product gas flows upward, it is contacted with a reflux liquid comprising condensed lights 7 from condenser 13. Gases and vapors that are not condensed in condenser 13 exit the condenser via condenser overhead stream 2, which is then split into recycle gas stream 14 and vent stream 15. Accordingly, the dehydration column functions to remove the majority of acrylic acid from reaction product feed stream 1, and to send the recovered acrylic acid via bottoms stream 16 for further treatment.

A portion of bottoms stream 16 from the dehydration tower is fed to a point near the top of second column (or finishing tower) 17 via second column feed stream 3. Another portion of bottoms stream 16 is fed to heat exchanger 12 via heat exchanger feed stream 20 and thus is recirculated to the dehydration column and is employed to cool the incoming hot reaction gas mixture. Either before or after junction 25 at which bottoms stream 16 is split, the pipe carrying bottoms stream 16 can be equipped with near IR probe 26 which is, in turn, connected by any conventional means (not shown) to a near IR spectrometer (not shown).

More than one near IR probe 26 can be used in the coupled, two-tower separation system and if more than one such probe is used, then the additional probe(s) is/are usually fitted to one or both of the pipes that carry condensed lights stream 7 and condensed overhead stream 4, respectively. Alternatively, IR probe 26 can be fitted to one or both of these other pipes to the exclusion of the pipe that carries bottoms streams 16. If near IR probe 26 is fitted to more than one of these pipes, then typically the signal from only one of the probes is used to create a signal that is sent to condenser 13 to control its operating temperature, and this probe is typically the probe that is monitoring the water content of bottoms stream 16. The other probes monitor the water content of the streams with which they interface, but the signal from these probes are not used to create a signal to condenser 13 for the purpose of controlling its operating temperature.

The liquid from second column feed stream 3 flows downward in the second column where it is contacted with rising vapors from reboiler 18. The second column preferably is a distillation column. The configuration of the distillation column is not particularly critical, and the column can be designed using criteria well known to those skilled in the art. Vapor phase overhead stream 8 from the second column is introduced into condenser 19, where the majority of the overhead stream is condensed. A small purge stream (not shown) of noncondensibles passes out of condenser 19 as a vent stream, which can be disposed of, recycled, or otherwise handled. Condensed liquid from condenser 19 is sent via condensed liquid stream 4 to heat exchanger 12, and then is sent to the dehydration column via cooling liquid stream 11 to cool the gaseous reaction mixture of stream 1. A portion of second column bottoms stream 9 is recirculated to the second column via reboiler 18. The remainder of bottoms stream 9 flows via residual stream 6 for further treatment, disposal, or a combination of these. For example, residual stream 6 can be sent to an esters unit, to a cracking unit, or to a combination of these.

Acrylic acid product stream 5 is taken from the second column as a side draw. The stream preferably is a vapor stream, but can be a liquid stream.

Figure 2:
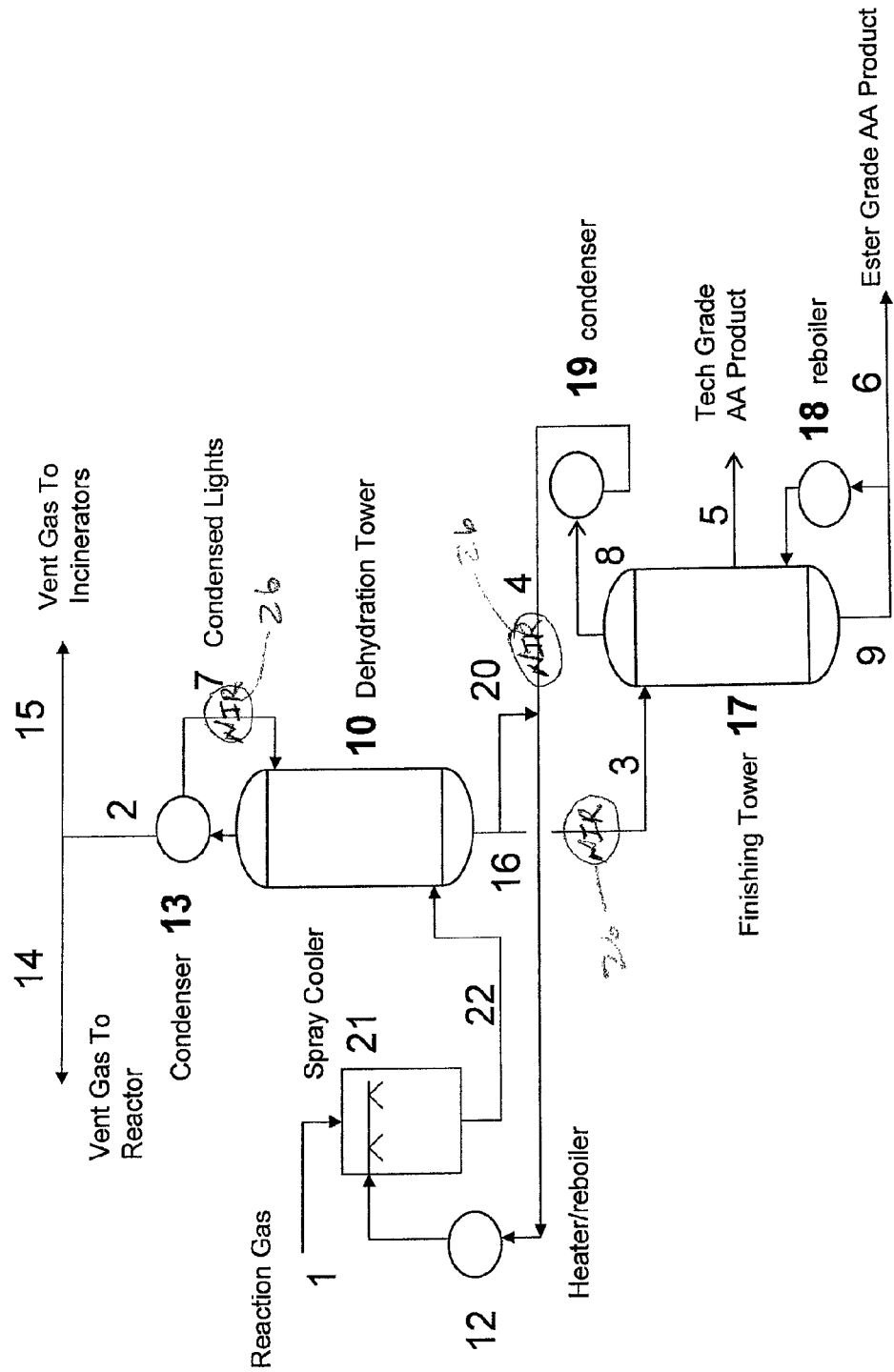
FIG. 2 is a schematic process flow sheet showing a configuration in which the quenching of the reaction product obtained from the gas-phase oxidation of at least one (meth) acrylic acid precursor is conducted primarily in a vessel located apart from the dehydration column.

FIG. 2 shows a variation of FIG. 1 in which the cooling of gaseous reaction product 1 is conducted primarily in a separate vessel prior to the dehydration column. In this embodiment, reaction gas mixture 1 enters spray cooler 21, and cooled reaction gas 22 is removed from the cooler and passed to the dehydration column for processing. In this embodiment, heater/reboiler (heat exchanger) 12 is relocated and fitted within the process scheme so as to receive dehydration column bottoms stream 20, and stream 4 from condenser 19 as feed streams.

Figure 3:
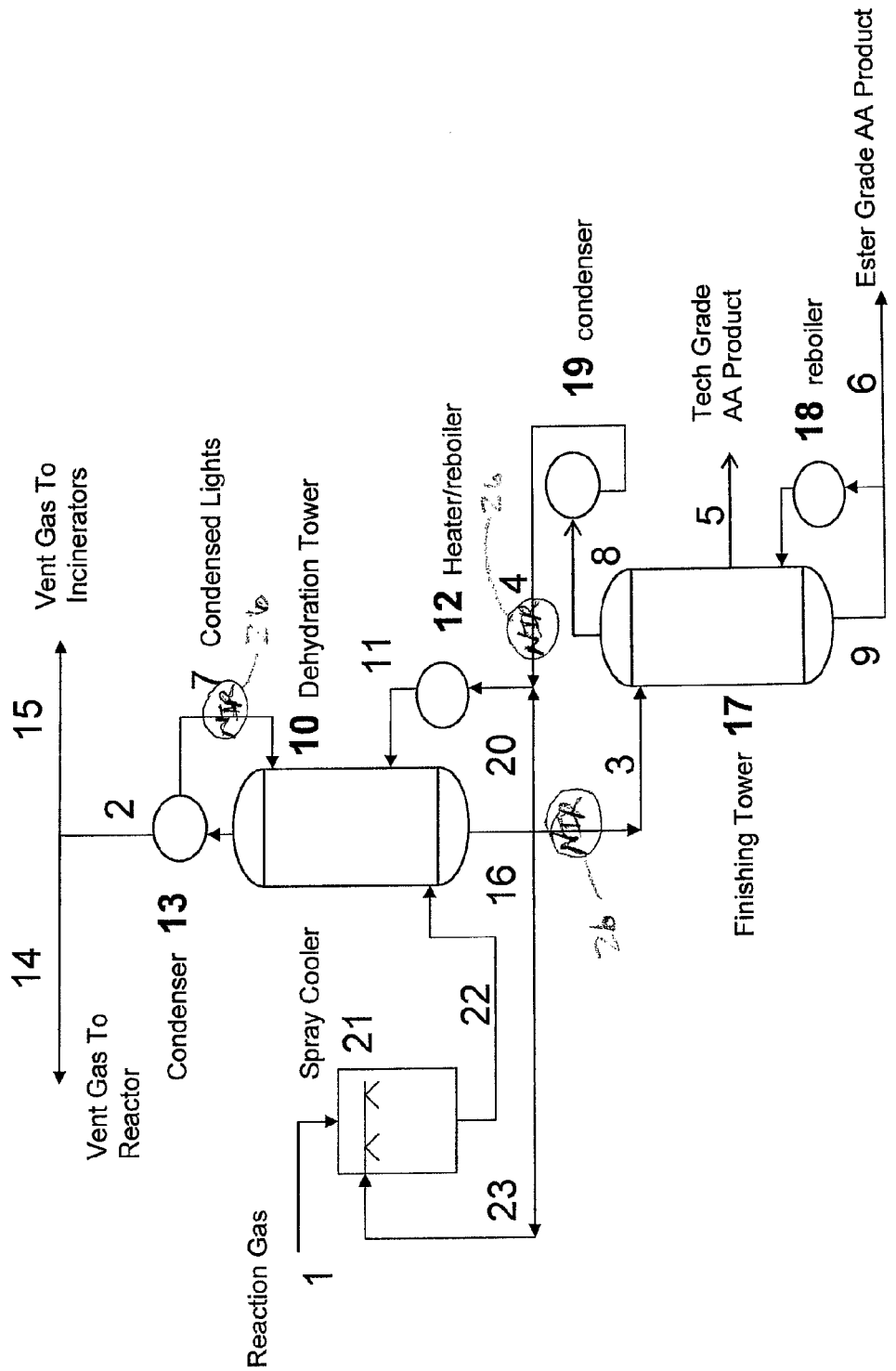
FIGS. 3 and 4 are schematic process flow sheets showing variations of the process shown in FIG. 2.

FIG. 3 shows a variation on FIG. 2 in which heater/reboiler 12 retains the same position that it has in FIG. 1, and the feed streams 23 to spray cooler 21 is now only a portion of dehydration column bottoms stream 16. The size of streams 16, 23, 20 and 4 can vary, usually with the size of stream 23 the largest. In this variation, reaction product gas stream 1 is subjected to a stepped cooling process, the first step occurring in spray cooler 21 and the next step in dehydration column 10, i.e., cooled reaction product gas stream 22 subjected to further cooling from liquid 11.

Figure 4:
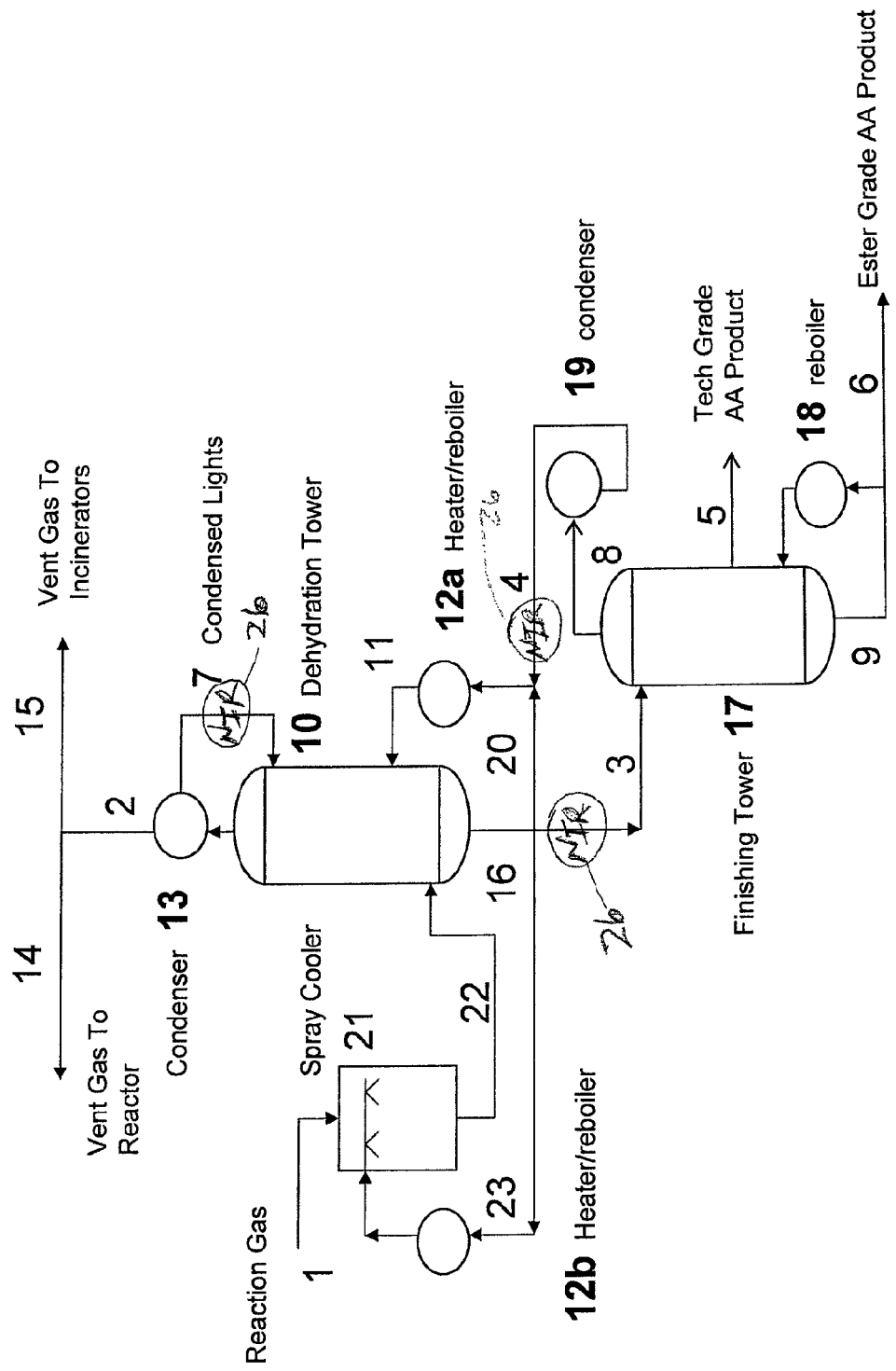

FIG. 4 shows yet another variation on FIG. 2 in which two heater/reboilers are employed, i.e., heater/reboilers 12*a* and 12*b*. The heater/reboilers can be the same or different in size and/or design, and heater/reboiler 12*a* is positioned and connected in essentially the same manner as heater/reboiler 12 in FIG. 1, and heater/reboiler 12*b* is positioned and connected in essentially the same manner as heater/reboiler 12 in FIG. 2.

FIG. 5 shows still another variation on FIG. 2, and in this instance surge tank 24 is positioned between dehydration tower 10 and finishing tower 17. The position of heater/reboiler 12 relative to spray cooler 21 varies from FIG. 2, but provides essentially the same function, i.e., to at least partially cool the hot, gaseous reaction product stream 1 before it enters into and is processed within dehydration column 10. Surge tank 24 is positioned such that it can receive a stream of dehydration column bottoms in times of excess flow, and then hold and/or pass these excess bottoms to finishing tower 17 for further processing.

One further embodiment (not shown in FIG. 5) comprises passing at least a portion of the bottoms from the dehydration column through at least one cooler prior to entering the surge tank. Furthermore at least a portion of the stream from the surge tank is passed through at least one pre-heater prior to entering the second column. Advantageously the at least one cooler and the at least one heater can be the same device (i.e., a process-to-process heat exchanger).

Although the invention has been described in considerable detail by the preceding examples and references to the drawings, this detail is for the purpose of illustration and is not to be construed as a limitation upon the spirit and scope of the invention as it is described in the appended claims.

We claim:

1. A coupled, two-tower distillation system for the dehydration of a reaction product obtained from the gas-phase oxidation of at least one (meth)acrylic acid precursor wherein the dehydrating is carried out without using solvent that forms an azeotrope with water, and whereby a side draw product stream of technical grade acrylic acid from the second column containing at least 98.5 wt % acrylic acid, less than 0.5 wt % water and less than 0.4 wt % acetic acid is produced, the system comprising (A) a first distillation tower equipped with a base and top, (B) a condenser coupled to and in open communication with the top of the first distillation tower, the condenser equipped with means for controlling its operating temperature wherein the means for controlling the operating temperature is configured to increase, decrease or maintain the operating temperature of the condenser based on a signal created by a near infrared spectrometer, (C) a second distillation tower equipped with a top, wherein the first distillation tower is connected to the second distillation tower such that a tails steam from the first tower is fed directly or indirectly into a top of the second tower while an overhead stream of the second tower is fed directly or indirectly into a base of the first tower (D) means for transferring dehydrated reaction product from the base of the first distillation tower to the top of the second distillation tower, and (E) a near IR spectrometer comprising a probe or flow cell positioned on or within the means for transferring dehydrated product from the base of the first distillation tower to the top of the second distillation tower, wherein the means for controlling the operating temperature of the condenser comprises a microprocessor that (i) receives a signal based on at least one of the water acetic acid and (meth)acrylic acid content of at least one of (i) a tails stream from the base of the first distillation tower and (ii) an overhead stream from the second distillation tower coupled to and that receives the tails stream from the first distillation tower, where said means for controlling operating temperature compares the signal against a pre-determined setpoint, said setpoint indicating a content of water, acetic acid, or (meth)acrylic acid.

2. The coupled, two-tower distillation system of claim 1 in which the means for transferring dehydrated reaction product from the base of the dehydration tower to the top of the finishing tower is a pipe.

3. The coupled two-tower system of claim 2 in which the condenser is a shell-tube condenser or a quench condenser.

* * * * *